US010076635B2

(12) United States Patent
Macy, Jr. et al.

(10) Patent No.: US 10,076,635 B2
(45) Date of Patent: Sep. 18, 2018

(54) METHODS AND DEVICES FOR ASEPTIC IRRIGATION, URINE SAMPLING, AND FLOW CONTROL OF URINE FROM A CATHETERIZED BLADDER

(71) Applicant: Hospi Corporation, Newark, CA (US)

(72) Inventors: Bradford Macy, Jr., Concord, CA (US); Igal Ladabaum, San Carlos, CA (US)

(73) Assignee: Hospi Corporation, Newark, CA (US)

( * ) Notice: Subject to any disclaimer, the term of this patent is extended or adjusted under 35 U.S.C. 154(b) by 515 days.

(21) Appl. No.: 14/747,972

(22) Filed: Jun. 23, 2015

(65) Prior Publication Data

US 2015/0290425 A1 Oct. 15, 2015

Related U.S. Application Data

(63) Continuation-in-part of application No. 13/414,205, filed on Mar. 7, 2012, now Pat. No. 9,060,752.
(Continued)

(51) Int. Cl.
| *A61M 39/16* | (2006.01) |
| *A61M 25/00* | (2006.01) |
| *A61F 5/442* | (2006.01) |
| *A61B 10/00* | (2006.01) |
| *A61M 39/10* | (2006.01) |
| *A61F 5/44* | (2006.01) |

(52) U.S. Cl.
CPC ....... *A61M 25/0017* (2013.01); *A61B 10/007* (2013.01); *A61M 39/105* (2013.01); *A61M 39/162* (2013.01); *A61F 5/442* (2013.01); *A61F 5/4405* (2013.01); *A61M 2025/0019* (2013.01)

(58) Field of Classification Search
CPC .... A61M 5/44; A61M 5/4404; A61M 5/4405; A61M 5/442; A61M 25/0017; A61M 39/162; A61M 39/225; A61M 2025/0019; A61M 2039/0018; A61B 10/007
See application file for complete search history.

(56) References Cited

U.S. PATENT DOCUMENTS

| 1,234,582 A | 7/1917 | Trueblood |
| 3,513,849 A | 5/1970 | Vaillancourt et al. |

(Continued)

FOREIGN PATENT DOCUMENTS

| EP | 2140903 A1 | 1/2010 |
| JP | 2002514475 A | 5/2002 |

(Continued)

*Primary Examiner* — Lynne Anderson
(74) *Attorney, Agent, or Firm* — Shay Glenn LLP

(57) ABSTRACT

A connector system includes a catheter connector port to attach to a urinary catheter, a urine exit port to connect to a urine collection device, an irrigation port to receive an irrigation syringe, and an internal valve. The irrigation port includes a pliable membrane that has a self-sealing opening to allow a tip of the syringe to extend therethrough. The internal valve cooperates with the syringe to shut off flow of fluid to the urine exit port when the syringe is inserted and allow for flow of fluid to the urine exit port when the syringe is removed. A distance between a proximal surface of the membrane and a distal end of the internal valve is such that the tip of the syringe can extend from a proximal end of the self-sealing opening to the distal end of the internal valve.

19 Claims, 13 Drawing Sheets

Related U.S. Application Data

(60) Provisional application No. 61/464,705, filed on Mar. 8, 2011.

(56) References Cited

U.S. PATENT DOCUMENTS

| | | | |
|---|---|---|---|
| 3,699,964 A | 10/1972 | Ericson | |
| 3,707,972 A | 1/1973 | Villari et al. | |
| 3,749,084 A | 7/1973 | Cucchiara | |
| 3,835,835 A | 9/1974 | Thompson et al. | |
| 3,965,910 A | 6/1976 | Fischer | |
| 4,476,866 A | 10/1984 | Chin | |
| 4,636,202 A | 1/1987 | Lowin et al. | |
| 4,655,747 A | 4/1987 | Allen | |
| 4,685,910 A | 8/1987 | Schweizer | |
| 4,723,943 A | 2/1988 | Spencer | |
| 5,095,723 A | 3/1992 | Lin | |
| 5,522,806 A | 6/1996 | Schonbachler et al. | |
| 5,527,297 A | 6/1996 | Paul | |
| 5,775,325 A * | 7/1998 | Russo | A61M 16/0463 128/202.27 |
| 6,165,168 A | 12/2000 | Russo | |
| 6,183,413 B1 | 2/2001 | Migachyov | |
| 6,245,048 B1 | 6/2001 | Fangrow et al. | |
| 6,344,033 B1 | 2/2002 | Jepson et al. | |
| 6,481,462 B2 * | 11/2002 | Fillmore | A61F 5/4405 137/607 |
| 6,663,590 B2 | 12/2003 | Blatter | |
| 6,913,244 B1 | 7/2005 | Atkinson et al. | |
| 7,056,301 B2 | 6/2006 | Liu | |
| 7,056,308 B2 | 6/2006 | Utterberg | |
| 7,150,740 B2 | 12/2006 | Bennett et al. | |
| 7,850,677 B2 | 12/2010 | Blake et al. | |
| 8,075,533 B2 | 12/2011 | Lee | |
| 9,060,752 B2 | 6/2015 | MacY, Jr. | |
| 2003/0195478 A1 | 10/2003 | Russo | |
| 2004/0079363 A1 | 4/2004 | Casper et al. | |
| 2006/0064065 A1 | 3/2006 | Russo | |
| 2006/0293640 A1 | 12/2006 | Greco | |
| 2010/0292672 A1 | 11/2010 | Lee | |
| 2011/0283996 A1 | 11/2011 | Abrams | |
| 2012/0277664 A1 | 11/2012 | Macy, Jr. | |
| 2014/0058320 A1 | 2/2014 | Hansen | |

FOREIGN PATENT DOCUMENTS

| | | |
|---|---|---|
| LU | 58599 A1 | 8/1969 |
| RU | 2116802 C1 | 8/1998 |
| SU | 1806770 A | 4/1993 |
| WO | WO 96/40359 A1 | 12/1996 |

\* cited by examiner

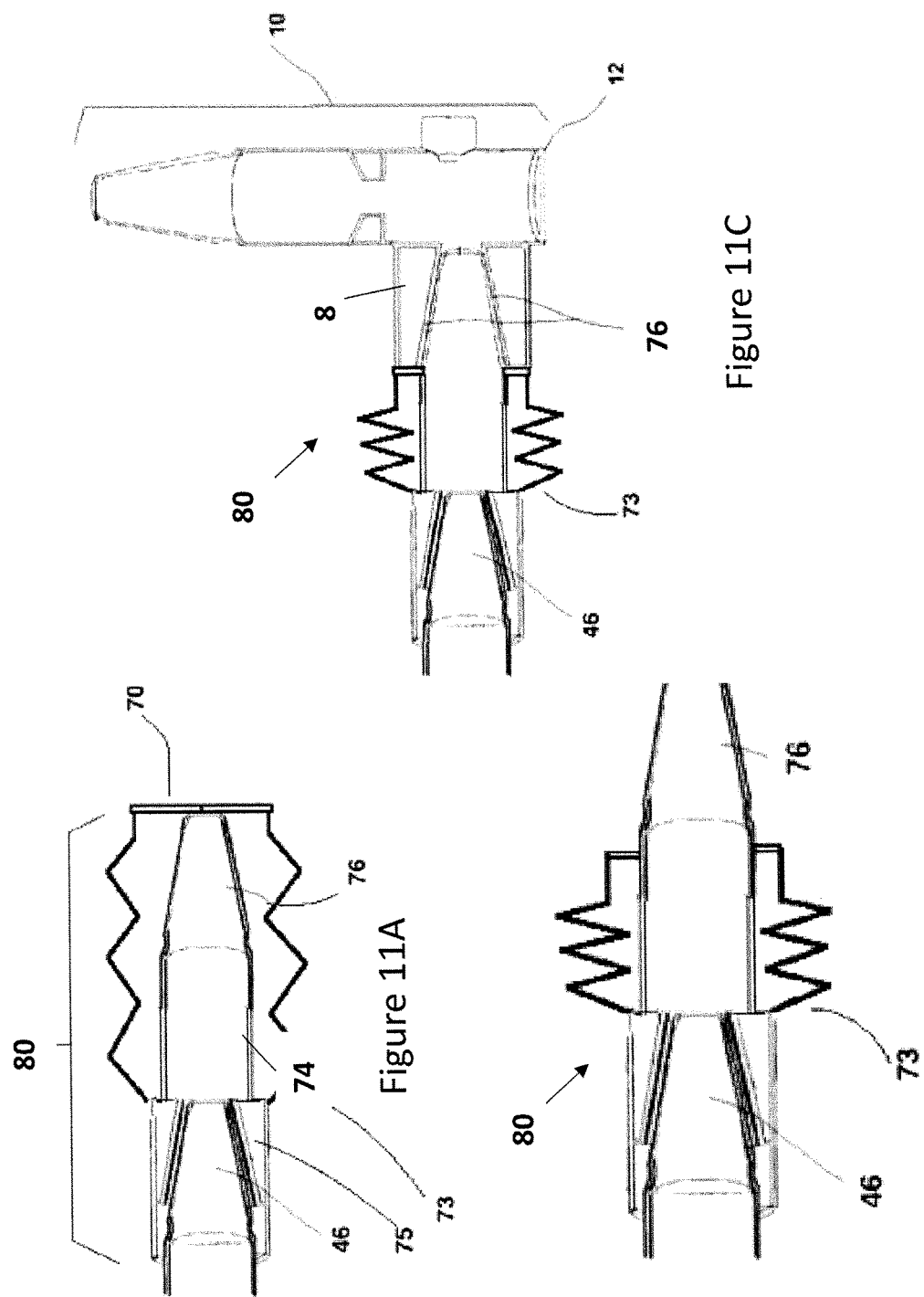

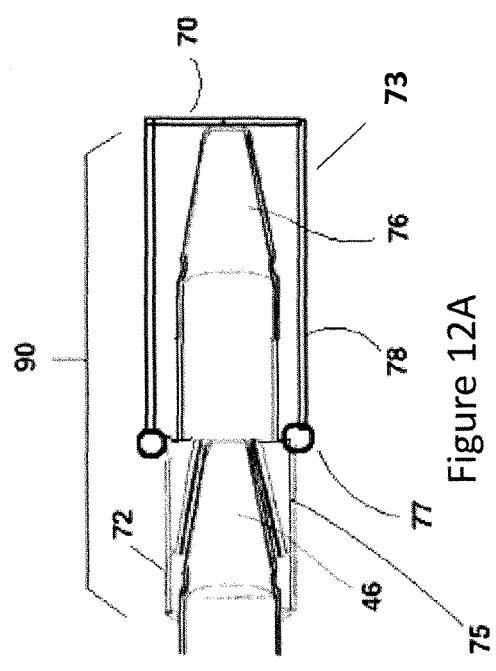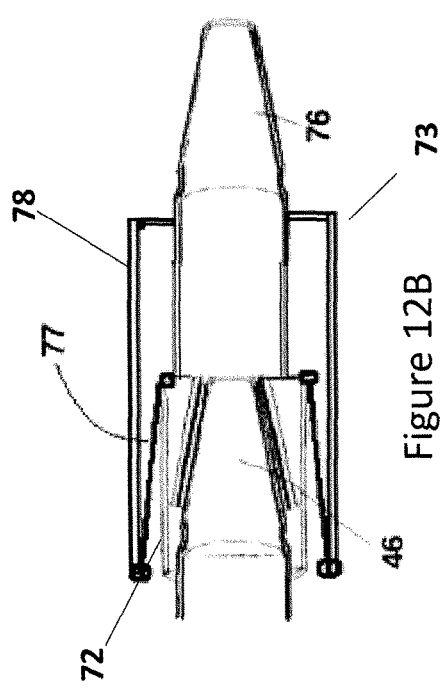

METHODS AND DEVICES FOR ASEPTIC IRRIGATION, URINE SAMPLING, AND FLOW CONTROL OF URINE FROM A CATHETERIZED BLADDER

CROSS REFERENCE TO RELATED APPLICATIONS

This application is a continuation-in-part of U.S. patent application Ser. No. 13/414,205, titled "METHODS AND DEVICES FOR ASEPTIC IRRIGATION, URINE SAMPLING, AND FLOW CONTROL OF URINE FROM A CATHETERIZED BLADDER," filed Mar. 7, 2012, now U.S. Pat. No. 9,060,752, which claims the benefit under 35 U.S.C. § 119 of U.S. Provisional Patent Application No. 61/464,705, titled "'SELF-CLOSING PORT AND VALVE ASSEMBLY' AN APPARATUS FOR IMPROVED IRRIGATION AND DRAINAGE OF THE CATHETERIZED BLADDER," filed Mar. 8, 2011, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This invention relates to methods, systems, and apparatuses to assist with the irrigation, urine sampling, and drainage of the catheterized bladder, and more particularly, but not limited to, aseptic methods, systems, and apparatuses to assist with improved irrigation, urine sampling, and drainage of the catheterized bladder.

BACKGROUND

Existing urinary catheter technology results in numerous health and safety issues for patients, medical personnel, and the community at large. The technology of indwelling urinary catheters has barely changed over the last 50 years. Improvements in existing urinary catheter systems are highly desirable. A urinary catheter drainage system is made up of the catheter itself, which is inserted into the bladder, and the urine collection device, which attaches to the catheter with tubing and collects the urine into a receptacle. One example of a urine collection device is a bedside drainage bag, which usually includes a tube connected to the catheter leading to a large bag that hangs on the bedside to collect the urine. Another example is a leg bag, which is worn when a patient is up and around and includes a shorter tube attached to a smaller bag that is attached to the leg and collects urine.

The complications associated with catheterization of the bladder include catheter associated urinary tract infections (CAUTI's), blockage (due to struvite or biofilm formation), bladder atony (causing a short term or permanent inability to void), bladder spasms, and thickening of the bladder wall from long term use.

In addition to direct patient complications, there are numerous safety issues related to current urinary catheter systems, both in the inpatient setting and in the home health setting. Present systems put clinicians at risk of occupational injury related to bio-hazardous waste exposure. Clinicians are frequently sprayed with urine when attempting to irrigate clogged catheters, such as when pressure from the irrigation syringe causes swelling of the catheter and spray back to occur. Because the current available catheter technology demands that the catheter be disconnected from the urine collection device in order to irrigate the system, leaking or spilling of urine often occurs during these procedures. When these spills and splashes occur, clinicians, other patients, and the community at large are put at risk for cross contamination and the spread of infection, including antibiotic resistant pathogens.

In summary, most of the problems listed above arise, at least in part, from two primary problems with existing catheter systems: (1) Current catheter systems do not allow for the maintenance of a closed, aseptic system; and (2) Current catheter systems do not allow the bladder to fill and empty in a normal fashion.

About 30% of CAUTI's are shown to be caused by intraluminal bacterial biofilm formation. The primary way that bacteria enter the inner lumen to cause infection is by entering the drainage end of the catheter and ascending the inner lumen to the bladder. The 2009 CDC Healthcare Infection Control Practices Advisory Committee (HICPAH) listed a closed urinary drainage system for all catheters as a high priority recommendation, essential for all healthcare organizations caring for patients with catheters. They found both older and more recent data indicating that disconnection of the urine collection device from the catheter is a risk factor for bacteriuria.

In order to maintain a closed urinary drainage system, the catheter generally should not be disconnected from the urine collection device. The most common reason for disconnecting the catheter from the urine collection device is when the catheter needs to be irrigated. Many catheters need to be irrigated several times a day, requiring disconnection of the catheter from the urine collection device and exposing the patient to infection and the clinician to bio-hazardous waste repeatedly.

In order to address the specific problem associated with closed irrigation of a catheter, Russo U.S. Patent Application Pub. No. US 2006/0064065 discloses a closed system irrigation connector for urinary catheters includes a silicone diaphragm that opens when an irrigation device is attached and closes when it is removed. However, the device of Russo does not provide for an aseptic irrigation procedure. In order to maintain an aseptic closed system, anything entering the system should be free of bacteria. This means that the system would ideally have entrance portals that are closed while not being accessed and that are fully sanitizable prior to access.

In order to effectively sanitize a surface, the surface should be easily and fully accessible to apply the needed friction and anti-infective agent. The surface should not have crevices or difficult to reach places, as asperities, steps and other such features can trap bacteria and grow biofilm while remaining shielded from the sanitizing effects of the alcohol swab. The plastic entrance port disclosed by Russo does not have a flat, easily sanitizable surface, but has a crevice that cannot be effectively sanitized. Bacteria hiding on this un-sanitizable surface can enter the system during irrigation and infect the patient.

The second major problem with current catheter systems is that they drain the bladder constantly, not allowing it to fill and empty in a normal manner. This leaves a pool of concentrated, stagnant urine in the neck of the bladder below the drainage holes on the catheter. This stagnant urine serves to create a perfect breeding ground for bacteria. Catheter blockage is another problem with "constant drain" catheter systems and is caused by the buildup of biofilm and salt crystals at the opening of the catheter. Much like a stalactite, the high pH, high mineral fluid in the neck of the bladder provides the perfect environment for this to occur. Bladder spasms can be caused by several factors associated with constant drain systems. The most frequent cause is CAUTI, as already discussed above. With CAUTI, the bladder wall becomes irritated and even swells, causing spasms. The loss of normal stretching and contracting of the detrusor can also cause spasms. Irritation from highly concentrated and high pH urine can also be factor. Bladder wall thickening has also been observed in long-term catheterizations and may be a result of the increasing retention of urine. Catheter-related bladder atony is another complication associated with not allowing the bladder to fill and empty. When the bladder no longer fills and empties in a normal fashion, the detrusor muscle can atrophy, causing a temporary or even permanent inability to void after catheterization. These problems could be solved, at least in part, by allowing the bladder to fill and drain in a more normal fashion.

Many types of valved catheters and universal connections exist that allow for intermittent draining and retention of the bladder. None of the prior art in this area discloses sanitizable surfaces on entry ports leading from the outside to the inside of the closed urinary drainage system. These prior art systems thus often complicate the problem by introducing bacteria into what should be a closed system. A system, method, and apparatus is needed that allows for aseptic irrigation and urine sampling while maintaining a closed system, while allowing for control of urine flow, permitting the bladder to fill and empty as needed or prescribed.

Moreover, disconnection of the urine collection device from the catheter is also desirable for many practical reasons, even if not required for aseptic irrigation and sampling. For example, the need to disconnect the urine collection device arises in the following situations, which can occur several times per day:
  1. When the drainage bag needs to be replaced with a new bag.
  2. When a patient changes the clothing or underclothing on the lower part of their body.
  3. When a patient switches from a bedside urinary drainage bag to a leg drainage bag or vice versa.
  4. When it is desirous to temporarily disconnect a urinary collection device from the catheter portion of the system for tests, transfers, bathing and numerous other purposes.
  5. When a patient must have a urinary catheter but desires to avoid being connected a urinary collection device for a given time period.

In order to reuse a urine collection device once it has been disconnected from the system, the connecting end of the urine collection device has to be fully protected from contamination and not come into surface contact with any other non-aseptic surface per the principles of asepsis. It is not adequate to simply swab an exposed unprotected end of a urine collection device that was disconnected from the system with a disinfectant prior to reconnection to the catheter end. This is because the urine collection device is open at the connection end, and bacteria can enter the inside of the urine collection device, which is not sanitizable. Reusable protective covers or sheaths are currently employed to cover the connecting end of the urine collection device when it has been disconnected from the catheter end of the system. However, these reusable covers are generally not adequate and tend to lead to contamination of the system. This is because the covers can be contaminated in between uses and are not sanitizable on the inside surface that comes into contact with the connecting end. As a result, the covers can introduce bacteria to the surface of the connecting end of the urine collection device.

An improved connector system is therefore needed to allow for aseptic disconnection and reconnection of the urine collection device from the catheter in all of the above circumstances while maintaining a closed urinary drainage system under these circumstances.

It is therefore desirable to provide an improved urinary drainage connector system that allows for aseptic disconnection and reconnection of the urine collection device from the catheter, in addition to a system that obviates the need for disconnection during irrigation/sampling.

SUMMARY OF THE DISCLOSURE

Systems, methods, and apparatuses for improved aseptic irrigation, urine sampling, and flow control of urine from the catheterized bladder are disclosed. The disclosed invention, also referred to for the purposes of easy reference only, as a port and valve assembly, allows for aseptic irrigation and urine sampling of the catheterized bladder without disconnecting the catheter from the drainage bag by including a sanitizable self-closing port and allowing for bypassing of the drainage bag during irrigation. An irrigation syringe, irrigating device, or urine sampling device can be inserted into a self-closing port on the apparatus to irrigate or urine sample the bladder without disconnection of the catheter from the urine collection device, and the bladder can be irrigated or urine sampled while maintaining a closed, aseptic system. When the syringe is removed, the port closes. The flat closed surface of the port is easily sanitizable with standard medical sanitizer, such as 70% alcohol, so bacteria cannot enter the system when a device is attached. This allows for aseptic access to the interior of the urinary catheter system so that irrigation can be performed without contamination of the urinary drainage system by bacteria or exposure to body fluids and infectious waste.

Another aspect of the invention employs an inner mechanism that prohibits shuts the flow of fluid to the urine collection device while an irrigation syringe, irrigation device, or collection device is inserted in the port. This mechanism allows for effective irrigation and urine sampling of the catheter and bladder without fluid or air being shunted into, or pulled from, the drainage collection device. Shutting flow off from the urine collection device is essential for irrigating a catheter that is attached to the urine collection device. If not done, fluid would flow into the collection device and not the catheter being irrigated. The system disclosed herein makes the collection of urine samples easy by sealing the urine collection device end, allowing for suction of urine from the bladder.

In yet another aspect, within some embodiments of the present invention, the system and apparatus has an externally controlled mechanism to shut off the flow of urine from the bladder to the urine collection device for a prescribed adjustable period of time, enabling the bladder to fill and empty in a more normal fashion. This feature is important because it allows clinicians to set the amount of time for bladder filling, without worrying about releasing the urine at a particular time, an important safety and convenience feature. This feature also allows for bladder training of patients, allowing for increased increments of time in which the bladder can fill with urine, thus slowly training the bladder to hold more urine before needing to empty.

The improved utilities of the present invention can decrease the chance of urinary tract infection or bladder atony, decrease the risk of blood and body fluid exposure, and greatly simplify the procedure of bladder irrigation of the catheterized patient.

One aspect of the invention provides a urinary catheter connector system having a housing, a catheter connector port supported by the housing and configured to attach to a urinary catheter, a urine exit port supported by the housing and configured to connect to a urine collection device, an irrigation port supported by the housing and configured to receive an irrigation syringe, a channel in the housing fluidly connecting the catheter connector port, the urine exit port and the irrigation port, and a valve supported by the housing and adapted to cooperate with the irrigation syringe to shut off flow of fluid and air to the urine exit port when the irrigation syringe is inserted and allow for flow of fluid and air to the urine exit port when the irrigation syringe is removed. In some embodiments, the valve has a first position in which the urine collection device is in fluid communication with the catheter connector port and a second position in which the urine collection device is not in fluid communication with the catheter connector port. The valve may be biased to the first position by, e.g., a spring. The valve may also be adapted to be moved from the first position to the second position by a syringe tip inserted into the irrigation port.

In some embodiments, the valve includes a thickening in the wall of the housing, wherein the thickening decreases the diameter of the channel and is configured to approximate the size of the tip of an irrigation syringe and to mate snugly with the irrigation syringe. When the irrigation syringe is inserted into the valve, the urine collection device is not in fluid communication with the catheter connector port, and when the syringe is not inserted in the valve opening, the urine collection device is in fluid communication with the catheter connection port. In some embodiments, the valve has a valve seat adapt to mate with an exterior surface of the irrigation syringe to shut off the flow of fluid and air to the urine exit port when the irrigation syringe is inserted and allow for the flow of fluid and air to the urine exit port when the irrigation syringe is removed.

Some embodiments of the invention also include a valve control mechanism adapted to move the valve from the first position to the second position without inserting a device into the irrigation port. The valve control mechanism may be adapted to automatically permit the valve to move from the second position to the first position after a time period without operator intervention. In some embodiments, the valve control mechanism includes a compliant balloon.

Some embodiments of the invention have a valve control mechanism with a compliant balloon adapted to be inflated to close the valve. Some such embodiments also include a compressible fluid-filled actuation chamber, first and second passages connecting the actuation chamber with the interior of the balloon, and a one-way valve disposed in the first passage to permit fluid flow from the actuation chamber into the balloon and block fluid flow from the balloon into the actuation chamber. The valve control mechanism may also have a syringe port adapted to permit inflation of the balloon by a syringe.

Some embodiments of the invention also have a pliable membrane extending over the irrigation port. The membrane has a self-sealing opening adapted to permit insertion of a syringe tip. In some embodiments, the irrigation port has an exterior surface that is flat and completely exposable to friction applied with a medical sanitizing agent so that the irrigation port is fully sanitizable. The irrigation port may connect to the channel between the catheter connection port and the urine exit port.

Another aspect of the invention provides a method of irrigating a urinary catheter, including the steps of: draining urine from an indwelling urinary catheter through a catheter connector port, a channel, and out through a urine exit port; simultaneously opening an irrigation port and closing off flow to the urine exit port; and injecting irrigation fluid through the irrigation port, the channel, the catheter connector port and into the catheter. In some embodiments, the irrigation port surface is sanitized prior to insertion of the irrigation syringe. In some embodiments, the method also includes the step of simultaneously closing the irrigation port and opening the urine exit port, thereby allowing urine to drain from the indwelling urinary catheter through the channel and out the urine exit port.

In some embodiments, the step of simultaneously opening the irrigation port and closing the urine exit port includes the step of moving a valve from a first position in which the urine exit port is in fluid communication with the catheter connector port to a second position in which the urine exit port is not in fluid communication with the catheter connector port. The moving step may include the step of moving the valve with a distal tip of a syringe. The method may also include the step of inserting the syringe through a self-sealing opening in the irrigation port.

In some embodiments, the step of simultaneously opening the irrigation port and closing the urine exit port includes the step of inserting a syringe through the irrigation port and into a valve. In some such embodiments, the step of simultaneously opening the irrigation port and closing the urine exit port further includes the step of seating an outside surface of the syringe in a valve seat of the valve.

Yet another aspect of the invention provides a method of operating a urinary catheter system including the following steps: establishing flow of urine from an indwelling urinary catheter through a connector and into a drainage bag; actuating a valve to stop the urine flow; and permitting the valve to automatically open after a time period without operator intervention.

In some embodiments, the actuating step includes the step of expanding a balloon to block flow through the connector. In some embodiments, the permitting step includes the step of permitting the balloon to deflate. In some embodiments, the expanding step includes the step of compressing a valve actuation chamber. In some embodiments, the expanding step includes the step of injecting fluid into the balloon with a syringe.

Still another aspect of the invention provides a method of operating a urinary catheter system including the following steps: establishing flow of urine from an indwelling urinary catheter through a connector and valve opening and into a urine drainage connector; inflating a balloon manually to stop the urine flow through the valve opening and drainage connector; and deflating the balloon manually to allow urine to flow through the valve opening and drainage connector.

Yet another aspect of the invention provides a urinary catheter system, including a urinary catheter port, a urine exit port, an irrigation port configured to receive an irrigation syringe, a channel connecting the urinary catheter port, urine exit port and irrigation port, and a valve adapted to cooperate with the irrigation syringe to shut off flow of fluid and air to the urine exit port when the irrigation syringe is inserted and allow for flow of fluid and air to the urine exit port when the irrigation syringe is removed.

In general, in one embodiment, a urinary catheter connector system includes a housing, a catheter connector port, a urine exit port, an irrigation port, a channel in the housing, and an internal valve. The catheter connector port is supported by the housing and is configured to attach to a urinary catheter. The urine exit port is supported by the housing and is configured to connect to a urine collection device. The irrigation port is supported by the housing and is configured to receive an irrigation syringe. The irrigation port includes a pliable membrane extending thereover. The pliable membrane has a self-sealing opening therein configured to allow a tip of the irrigation syringe to extend therethrough. The channel fluidly connects the catheter connector port, the urine exit port, and the irrigation port. The internal valve is supported by the housing and adapted to cooperate with the irrigation syringe to shut off flow of fluid and air to the urine exit port when the irrigation syringe is inserted and allow for flow of fluid and air to the urine exit port when the irrigation syringe is removed. A distance between a proximal surface of the membrane and a distal end of the internal valve is selected such that the tip of the irrigation syringe can extend from a proximal end of the self-sealing opening to the distal end of the internal valve when the irrigation syringe is inserted into the irrigation port.

This and other embodiments can include one or more of the following features. The internal valve can include a thickening in the wall of the housing. The thickening can decrease the diameter of the channel and can be configured to approximate the size of the tip of the irrigation syringe and to mate snugly with the irrigation syringe. When the irrigation syringe is inserted into the internal valve, the urine collection device may not be in fluid communication with the catheter connector port, and when the syringe is not inserted into the internal valve, the urine collection device may be in fluid communication with the catheter connector port. The internal valve can include a valve seat adapted to mate with an exterior surface of the irrigation syringe to shut off the flow of fluid and air to the urine exit port when the irrigation syringe is inserted and allow for the flow of fluid and air to the urine exit port when the irrigation syringe is removed. The proximal surface of the pliable membrane can be flat and completely exposable to friction applied with a medical sanitizing agent so that the irrigation port is fully sanitizable. The irrigation port can connect to the channel between the catheter connection port and the urine exit port. The pliable membrane can be without crevices. A pliable membrane can extend over the urine exit port. The pliable membrane of the urine exit port can have a self-sealing opening therein configured to allow a tip of the urine collection device connector to extend therethrough. The pliable membrane of the irrigation port can be smooth and uniform. The system can further include an internal valve supported by the housing at the urine exit port that is configured to allow flow of liquid through the urine exit port when open and to prohibit the flow of fluid therethrough when closed.

In general, in one embodiment, a urinary catheter connector system includes a housing, a catheter connector port, a urine exit port, an irrigation port, and a channel. The catheter connector port is supported by the housing and is configured to attach to a urinary catheter. The urine exit port is supported by the housing and is configured to connect to a urine collection device. The urine exit port includes a first pliable membrane extending thereover. The first pliable membrane has a self-sealing opening therein configured to allow a tip of a urine collection device connector to extend therethrough. The irrigation port is supported by the housing and is configured to receive an irrigation syringe. The irrigation port includes a second pliable membrane extending thereover. The second pliable membrane has a self-sealing opening therein configured to allow a tip of the irrigation syringe to extend therethrough. A channel in the housing fluidly connects the catheter connector port, the urine exit port, and the irrigation port.

The urinary connector system can further include an internal valve supported by the irrigation port housing and adapted to cooperate with the irrigation syringe to shut off flow of liquid to the urine exit port when the irrigation syringe is inserted and allow for flow of liquid to the urine exit port when the irrigation syringe is removed. The system can further include an adaptor including a proximal end configured to removably attach to the urine collection device and a distal end that includes the urine collection device connector. The adaptor can include a housing with a sanitizable slit membrane disposed over the distal end. The adaptor can include a sleeve covering the urine collection device connector. The sleeve can be configured to retract to expose the urine collection device connector. The sleeve can include accordion or telescoping features configured to allow the sleeve to retract. The urinary connector system can further include an internal valve supported by the urine exit port housing and adapted to cooperate with the tip of the urine collection device connector to allow flow of liquid through the urine exit port into the urine collection device when open and to shut off flow of liquid to the urine exit port when closed. The internal valve can include an external feature configured to allow manual activation of the valve. The internal valve can be a spring valve or a flap valve. The system can further include a rigid cap configured to cover and mate with the tip of the urine collection device connector. The rigid cap can be configured to be removed from the urine collection device connector for insertion of the connector into the urine exit port and to be replaced when the connector is removed from the urine exit port. The rigid cap can further include a slit-valve positioned over a proximal end of the rigid cap to seal an inner space within the rigid cap.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 10A shows the connecting end of the urinary collection device not attached to the sheath. FIG. 10B shows the connecting end of the urinary collection device attached to and protected within the sheath.

FIGS. 11A-11C show an adaptor configured to mate to the urinary collection device and also configured to provide a compatible mating feature for the port and valve assembly. FIG. 11A shows the adaptor connected to the urinary collection device and covering the end of the device. FIG. 11B shows the adaptor connected to the urinary collection system and in its retracted state ready for connection to the port and valve assembly. FIG. 11C shows the adaptor connected to both the urinary collection device and the port and valve assembly.

FIGS. 12A and 12B show an alternate embodiment of the adaptor with a retractable protective sheath. FIG. 12A shows the adaptor connected to the urinary collection device and covering the end of the device, and FIG. 12B shows the adaptor connected to the urinary collection system in its retracted state ready for connection to the port and valve assembly.

FIG. 13A shows the valve closed, while FIG. 13B shows the valve open.

DETAILED DESCRIPTION

Figure 1:
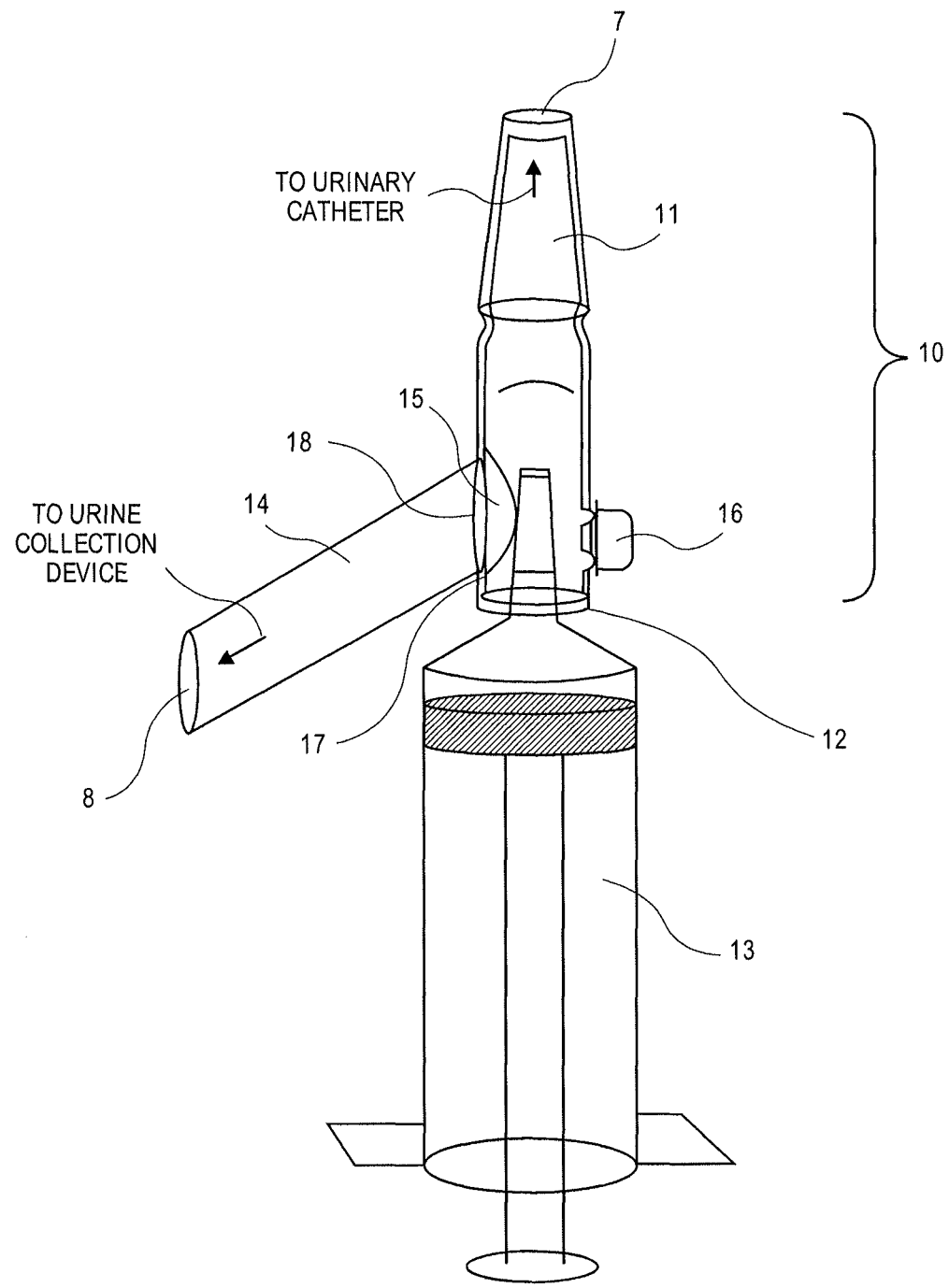
FIG. 1 is an illustration of a self-closing port and valve assembly according to one embodiment of the invention showing an irrigating syringe inserted into a self-closing port and bypassing the urine collection device through means of a valve, which closes flow to the urine collection device when the irrigation device is attached.

The following description and drawings are illustrative and are not to be construed as limiting. Numerous specific details are described to provide a thorough understanding. However, in certain instances, well known or conventional details may not be described in order to avoid obscuring the description. In accordance with the present invention, a novel and improved system for aseptic irrigation and urine specimen collection and/or for disconnection of urine collection device from a catheterized bladder is provided.

The devices, systems, and methods described herein solve the problem of disconnection and potential exposure to contaminants during irrigation and urine sampling by providing a port valve assembly that attaches at one port to the catheter, at a second port to the urinary collection device, and at a third port to an irrigation/sampling syringe. Some or all of the ports can be protected by slit membranes. The slit membranes described herein can advantageously be sanitized by swabbing 70% alcohol or other medical disinfectant across its surface prior to the sterile irrigation/sampling or the urine collection device connector syringe entering the system, thus providing for aseptic means to: (1) irrigate the catheter or sample urine without disconnecting the urine collection device during the irrigation/sampling; and/or (2) disconnect and reconnect the urine collection device. The slit membranes can close automatically after removal of the syringe or urine collection device connector, leaving the system closed and aseptic.

In some embodiments described herein, the port and valve assembly can include three ports. The first port connects directly to the catheter.

The second port, the urine exit port, connects to the urinary collection device. The second contains a valve that opens when the urinary collection device is connected and closes, shutting off fluid communication with the outside, when the urine collection device is disconnected from the port. The second port of the assembly can be protected by a slit membrane. The slit membrane ensures that the catheter side of the drainage system remains aseptically closed. It can be sanitized by swabbing 70% alcohol or other medical disinfectant across its surface. The outer surface of the slit membrane assembly is designed to be smooth, uniform, and free of crevices so that it can be fully sanitized. By placing a swabbable slit membrane on the urine exit port of the port and valve assembly, the urinary collection device can be disconnected and a closed aseptic system is preserved on the catheter end. In the preferred embodiment, the swabbable slit membrane is designed to also serve as the valve on the port. In other embodiments, the slit membrane is just protective, and the valve function (i.e., allowing fluid to flow in and out of the port) is provided by an internal valve.

The third port of the assembly, the irrigation and sampling port, contains a valve that closes fluidic communication with the collection system when an irrigation/sampling syringe is inserted into the port. The third port can also protected by a slit membrane. The third port's slit membrane can be sanitized by swabbing 70% alcohol or other medical disinfectant across its surface prior to the sterile irrigation/ sampling syringe entering the system, thus providing for aseptic means to irrigate the catheter or sample urine without disconnecting the urine collection device during the irrigation/sampling. Upon removal of the syringe, fluidic communication with the urine exit port is automatically re-established, and the slit membrane closes automatically, leaving the system closed, without fluidic communication to the outside.

Other embodiments can include few valves or ports and/or the valved assembly can be used with an adaptor that provides a connection between the urine collection device and the port and valve assembly.

Figure 2:
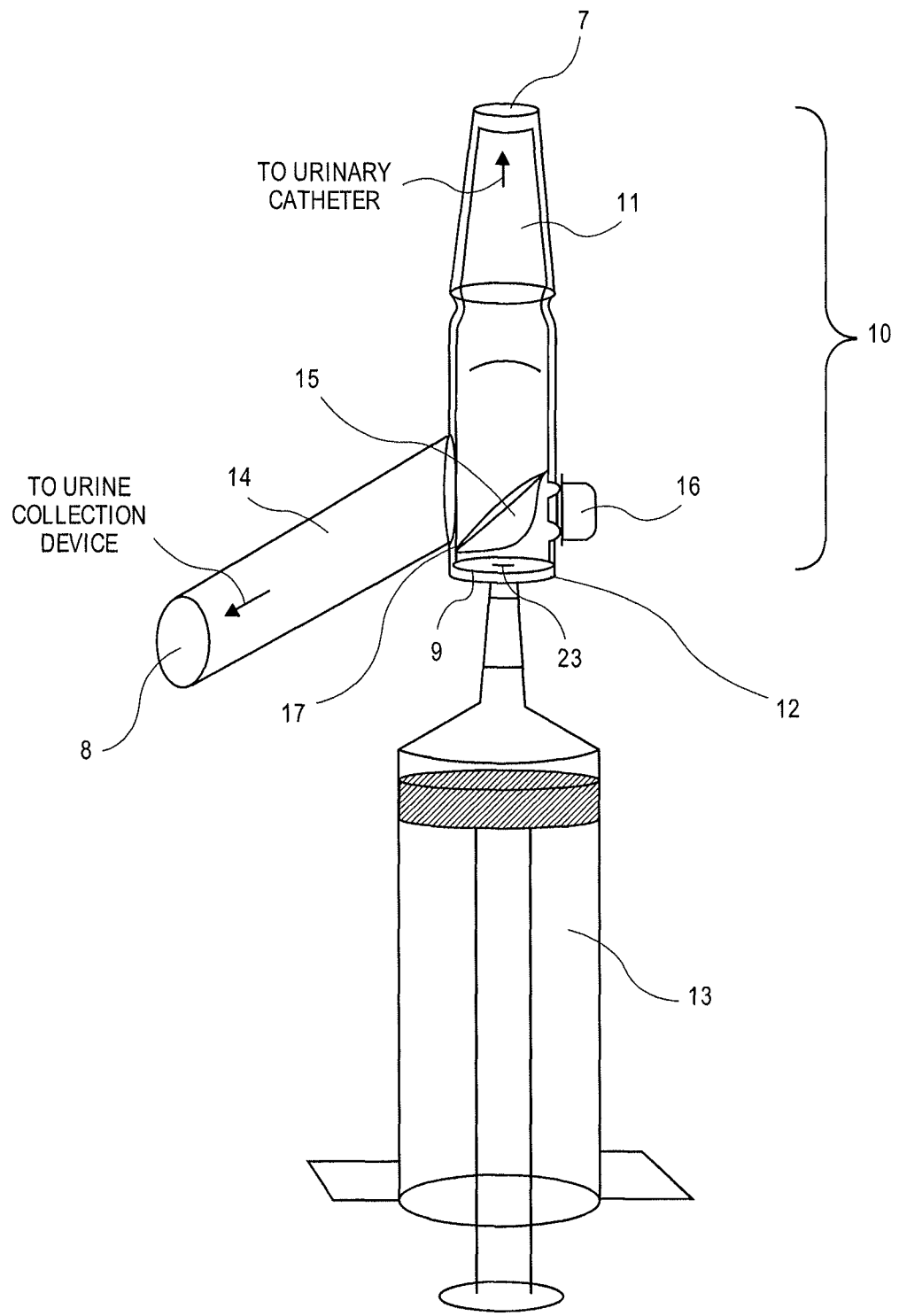
FIG. 2 is an illustration of a self-closing port and valve assembly showing the device of FIG. 1 without an irrigating syringe inserted into the self-closing port. Here, the valve is open, and urine can flow into the urine collection device.

FIGS. 1 and 2 are illustrations of a self-closing port and valve assembly 10 according to one embodiment of the present invention. Within this embodiment, the device has a fully sanitizable self-closing irrigation port 12 that allows a urinary catheter to remain attached to a urine collection device while being irrigated without disconnecting the urine collection device drainage tubing 14 from the urinary catheter (not shown). This allows for an aseptic, closed system, which keeps bacteria from entering the catheter and also prevents exposure to body fluids during the irrigation or sampling process.

The self-closing port and valve assembly 10 can be located in numerous places on a urinary catheter drainage system. For instance, it can be a part of a urinary catheter itself. It can be a separate device that connects between the catheter and the drainage bag. It can be a part of the urine collection device. In the embodiment of FIGS. 1 and 2, the assembly is a part of the urine collection device and is located at the junction between the catheter connector port 7 in the catheter connector 11 and the urine exit port 8 in the drainage tube 14, which drains urine from the catheter into the urine collection device.

In the embodiment of FIGS. 1 and 2, an internal valve 15 has a tension spring 17. The spring tension keeps the internal valve biased in a first position, in which a urine exit channel 18 is open to the urine drainage tube 14. Spring 17 can be, for example, a torsion spring, leaf spring or any other spring or spring-like element. Insertion of a catheter tip, irrigation syringe, or other similar device 13 into the self-closing irrigation port 12 pushes the internal valve 15 to a second position against the urine exit port to the urine collection device drainage tube 14, closing it off and bypassing any flow to the drainage tube while keeping the irrigation port open.

In the present embodiment, the valve 15 is fashioned so that a portion of it protrudes into the path of a device 13 inserted into the self-closing irrigation port 12. The device inserted into the port pushes the protruding portion of the valve in the direction of the urine exit port, closing the valve when the device is inserted into the irrigation port. This automatically shuts off the flow of fluid and air to the drainage bag, allowing for irrigation of the catheter and bladder without the irrigation fluid entering the drainage tube. When the irrigation procedure is complete and the syringe 13 is removed, the spring 17 moves the valve back to the open position to allow urine to flow from the catheter, into the urine collection device and to the drainage collection receptacle.

In the embodiment of the device in FIGS. 1 and 2, the port and valve assembly 10 also has a valve control mechanism 16 to externally shut the valve 15 without the insertion of a syringe or other object into the port 12. This would allow the valve 15 to be closed even when not irrigating or collecting samples from the catheter. Keeping the valve closed would stop the flow of urine from the bladder to the urine collection device drainage tube 14 and allow the bladder to fill with urine, an important physiological function that is normally inhibited in state of the art urinary catheter systems. In some embodiments, the valve control mechanism 16 may be designed in such a way as to allow for the valve to stay closed for a specific prescribed and adjustable amount of time, allowing for the bladder to fill for a prescribed amount of time and then empty when that time period ends. Examples of the valve control mechanism are described below.

Figure 3:
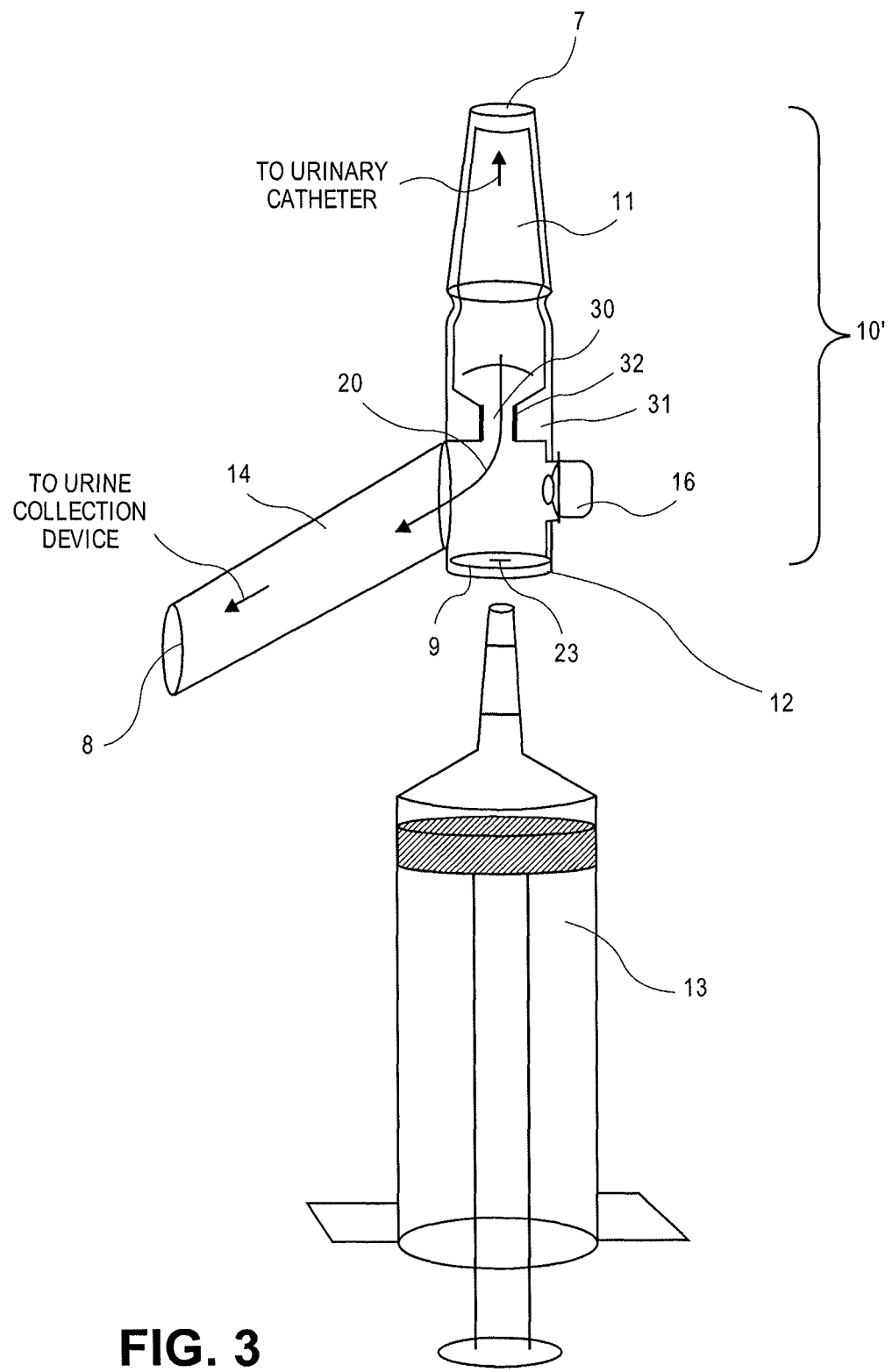
FIG. 3 is an illustration of a preferred embodiment of a self-closing port and valve assembly according to another embodiment of the invention. Here, there is no irrigating syringe inserted into the self-closing port, and urine can flow into the urine collection device.
Figure 4:
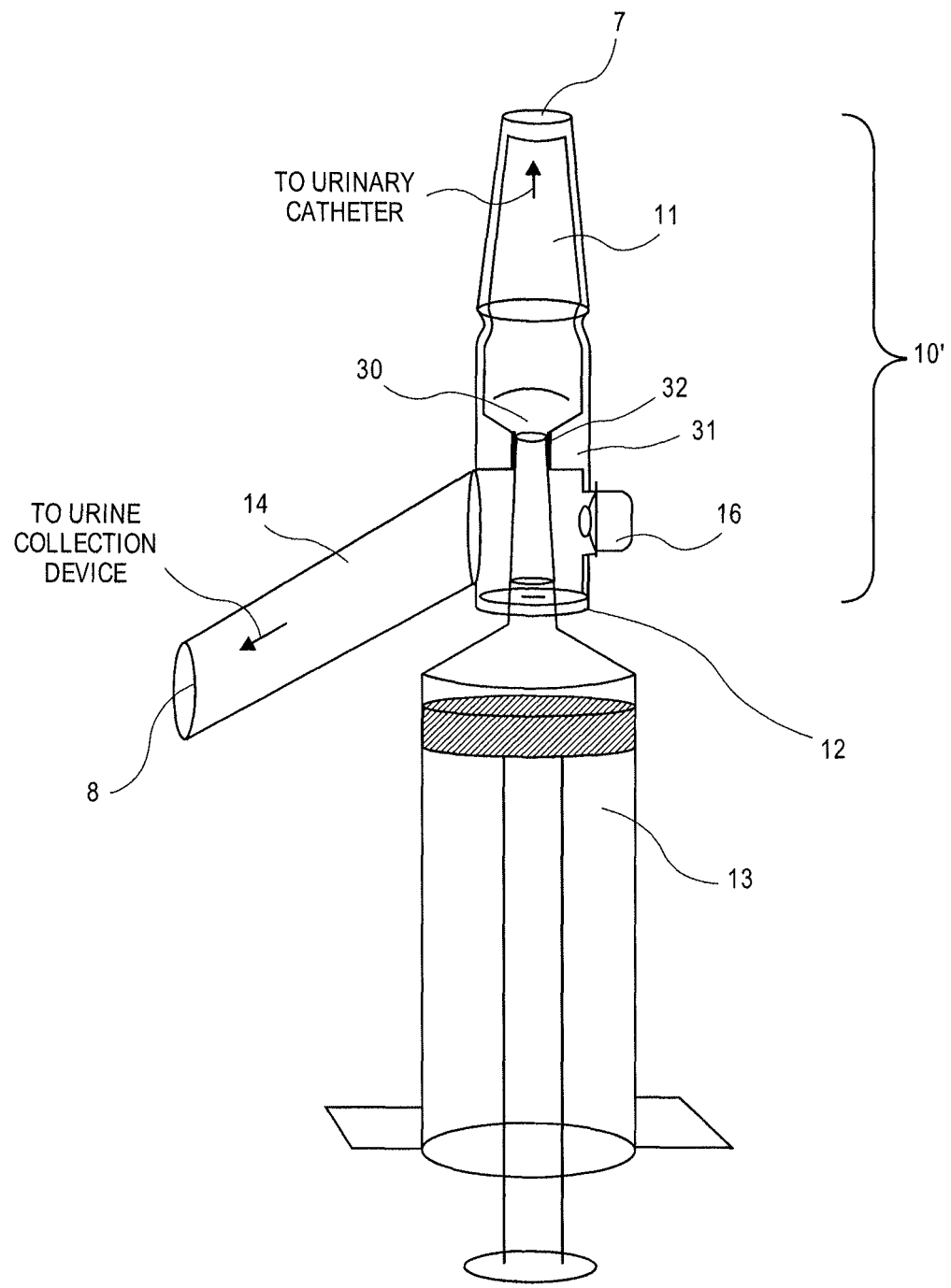
FIG. 4 is an illustration of a self-closing port and valve assembly showing the device of FIG. 3 with an irrigating syringe inserted into the self-closing port and bypassing the urine collection device through means of a valve that closes flow to the urine collection device.

FIG. 3 is an illustration of an alternative embodiment of the port and valve assembly 10'. In FIG. 3, a syringe is not inserted through a self-closing port, and fluid 20 is free to flow through an internal valve 31 through an opening in the valve 30. In FIG. 4, the flow of fluid to the drainage bag is shut off when an irrigation syringe is inserted into the port and valve assembly by means of an internal valve 31, which mates with the tip of the irrigation syringe when inserted. The tip of the irrigation syringe fits snugly into the internal valve, sealing flow of fluid or air from the drainage bag.

The internal valve 31 in the embodiment of FIG. 3 and FIG. 4 is made by a thickening in the wall of the port and valve assembly, which decreases the diameter of the channel, forming the valve opening 30. The internal valve 31 created by the thickened wall may, in some embodiments, be lined with a flexible material, such as foam, latex, or silicone, to form a valve seat 32 adapted to cooperate with an exterior surface of the syringe. When an irrigation device is inserted through the irrigation port, it enters the valve opening, and the syringe compresses the expandable material 32 lining the internal valve. The syringe is held tightly in place by this compression and creates an air and fluid seal.

Figure 7:
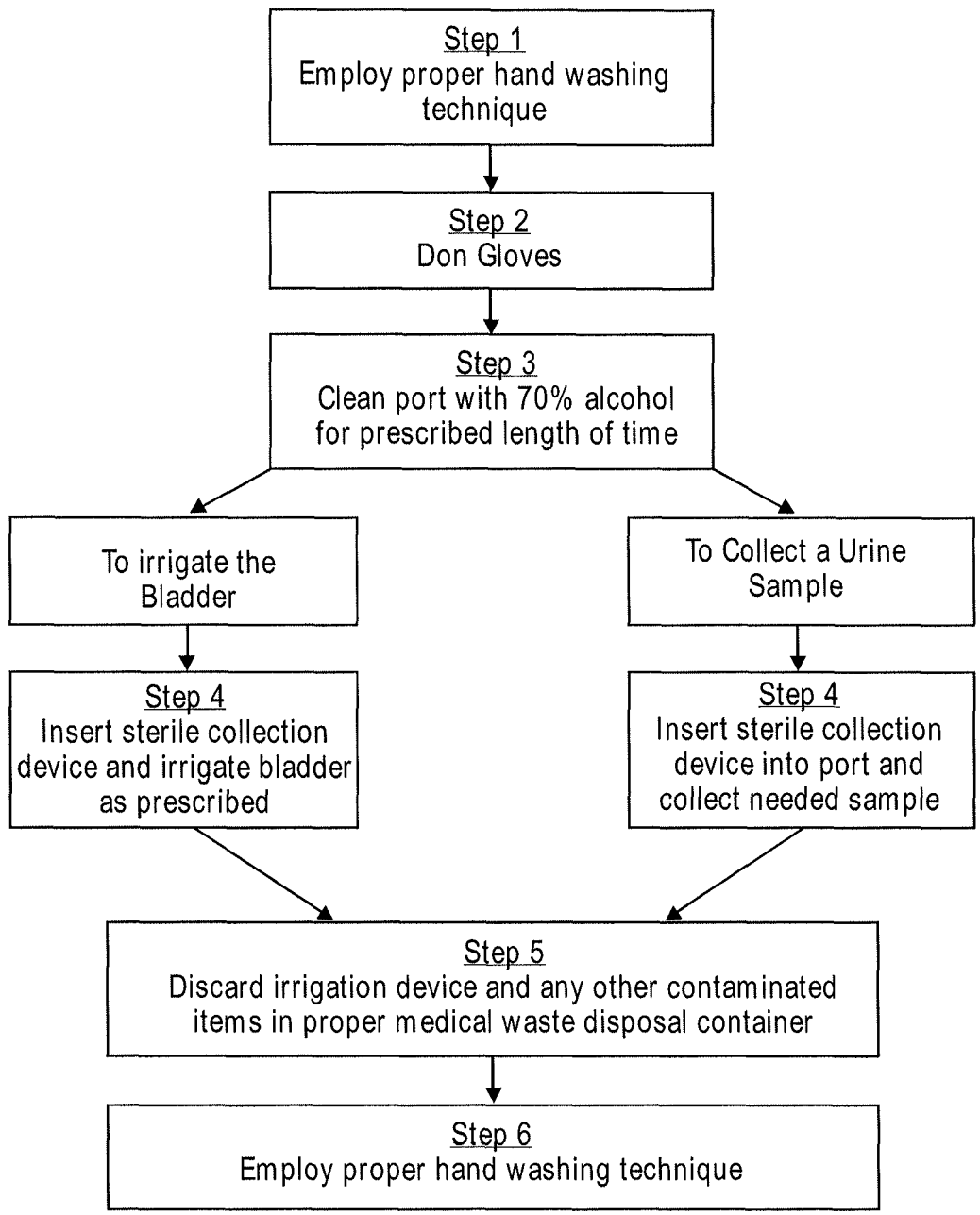
FIG. 7 is a flow diagram showing an aseptic port access procedure for irrigating or collecting a urine specimen from a port and valve assembly.

Referring to FIG. 3, the irrigation port 12 can include a self-sealing membrane 9 made of latex or other highly flexible and pliable material extending thereover. The membrane 9 is smooth and uniform (i.e., flat or without crevices), thereby making the entire surface (including attachment points to the port 12) smooth and uniform. Further, the membrane 9 has a small pliable hole within in the center that runs from the external portion of the membrane 9 to the internal portion of the membrane 9. When a syringe or other irrigation device is pushed against the external portion of the membrane 9, the pliable hole 23 spreads open, and the irrigation device can be passed through the membrane 9 to the internal portion of the port. When the syringe is removed, the hole 23 closes tightly, forming a seal that keeps urine in and bacteria out of the urinary drainage system. The smooth and uniform surface of the port 12 is easily sanitizable with 70% alcohol or other standard medical sanitizer, allowing for aseptic port access without introduction of bacteria into the drainage system. FIG. 7 is a flow diagram of an aseptic port access procedure.

Figure 5:
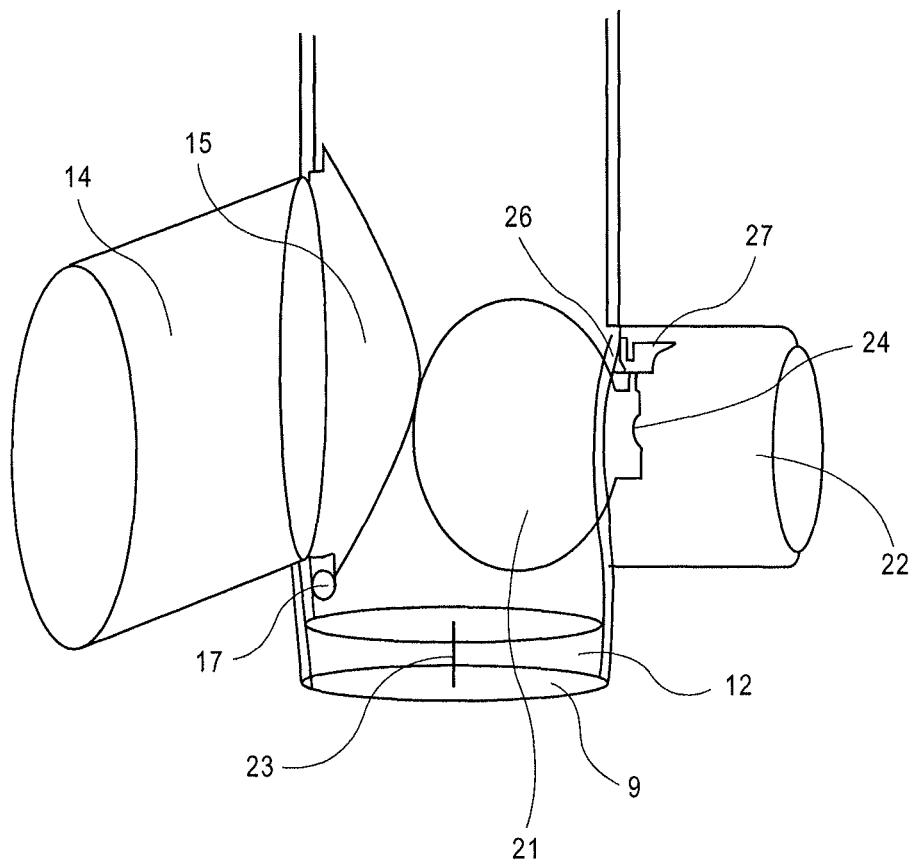
FIG. 5 is a detail of a port and valve assembly showing one embodiment of an optional valve actuator being used with the assembly shown in FIGS. 1 and 2.

The embodiment of the valve control mechanism shown in FIG. 5 consists of a small compliant balloon 21 which is inflated by an air filled chamber 22 that is made of a soft compressible material. By applying pressure to the air filled chamber manually, typically with the push of a finger or thumb, air is squeezed out of the chamber and into the balloon, which, in turn, closes the valve stopping the flow of urine out of the bladder. The chamber is fashioned in such a way as to allow air to pass without resistance into the balloon through a one way valve 24. Once inside the balloon, the air must pass through a block 27 in which one or more holes form a balloon deflation orifice. The time period over which balloon 21 deflates can be controlled by the size and/or number of holes in block 27, which allows for control of the amount of time the valve 15 stays open. The air passes through the block and out the air exit hole 26.

FIG. 6 is an illustration of an embodiment of a valve control mechanism for use with the port and valve assembly of FIGS. 3 and 4. This figure demonstrates how the balloon 21 inflates to close off the flow of fluid from the catheter to the drainage bag by blocking flow from the opening 30 to the urinary drainage end of the port and valve assembly.

Figure 6A:
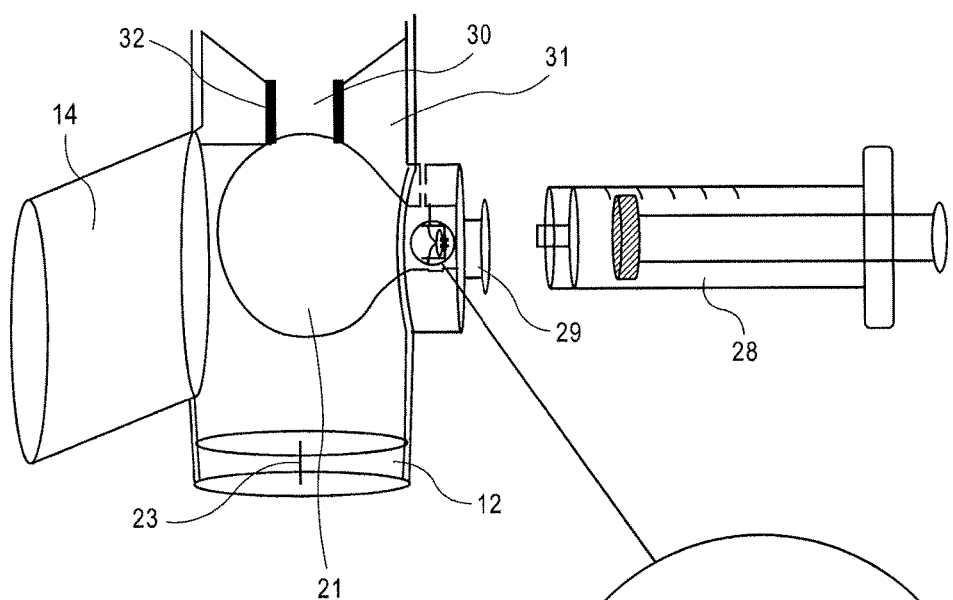
FIGS. 6A and 6B show another embodiment of an optional valve actuator being used with the assembly shown in FIGS. 3 and 4.
Figure 6B:
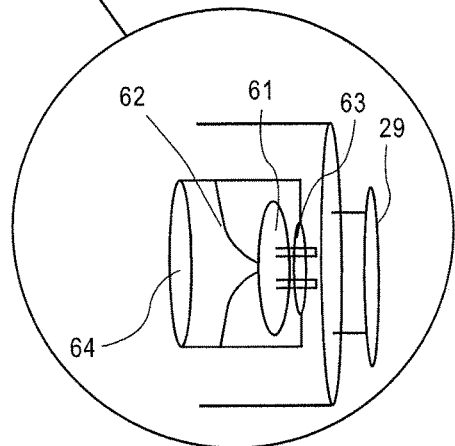

In other embodiments, the balloon may be inflated by other means, such as a syringe. FIGS. 6A and 6B show one embodiment of the port and valve assembly, in which the compliant balloon is inflated by a syringe 28. Air or fluid is introduced into the balloon by the syringe, which attaches onto a luer locking connection 29 that has a valve 61 attached to a spring 62. When the syringe is attached, it pushes prongs 63 on the surface of valve 61, depressing the valve and spring and opening a fluid connection between the syringe and balloon cavity 64. When the syringe is removed, the spring pushes the valve closed, sealing the compartment and trapping the air or fluid within the balloon, keeping it inflated. In order to restart the flow of urine from the bladder to the urinary drainage bag, a syringe is simply re-attached to the luer locking port and the air or fluid is removed from the balloon.

In some embodiments, the air in the balloon slowly leaks out through a different air passage 26 from which it entered and through a block 27 with one or more holes, as described above. The valve control mechanism 16 in some embodiments may employ a lever instead of a balloon that pushes the valve shut.

Figure 8:
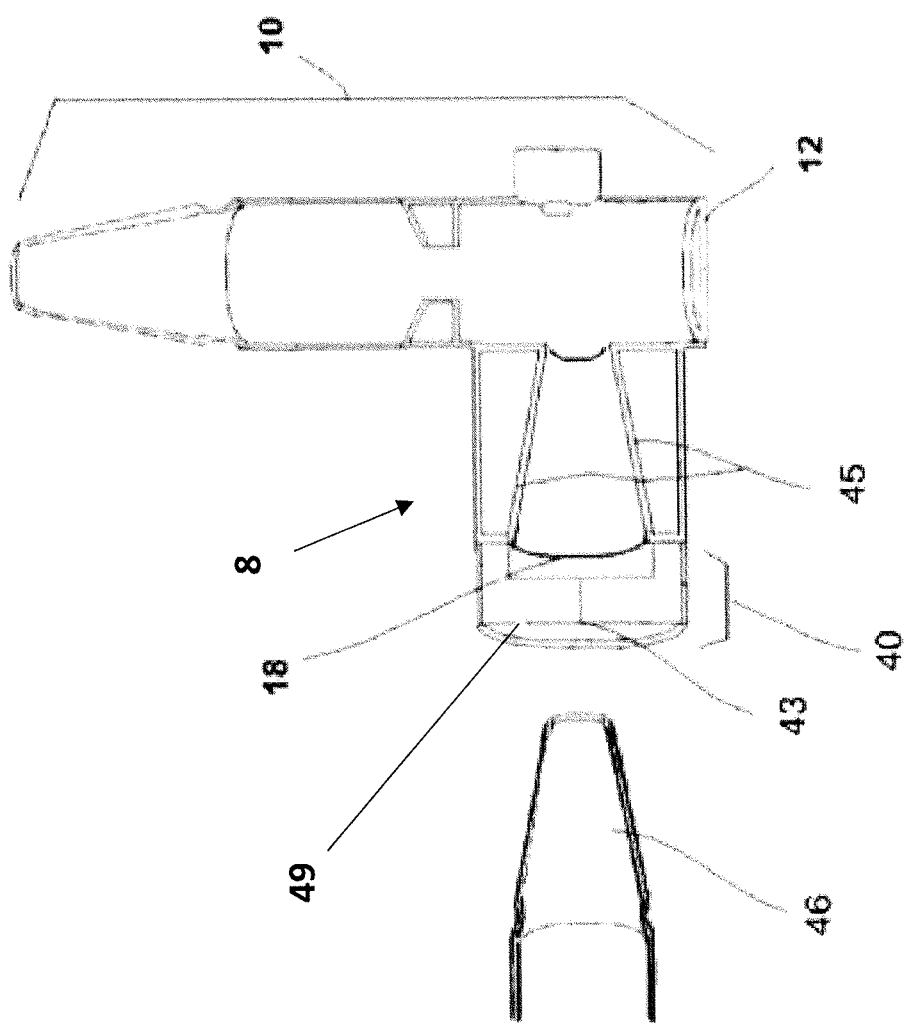
FIG. 8 is a cross section of one embodiment of a port and valve assembly having a sanitizable self-closing port with flexible valve body at the urine exit port. The urine collection device connector is not connected to the port.

In some embodiments, the port and valve assembly described herein can further include a slit-valve on the urine collection port. Referring to FIG. 8, a connector 10 includes, in addition to the self-closing slit membrane 9 of the irrigation and sampling port 12, a self-closing slit-valve 40 on the urine exit port 8 at the proximal end of the urine exit channel 18. The slit-valve 40 is similar in function and design to the slit membrane on port 12 and is likewise a fully sanitizable self-closing valve extending over the port 8. The valve 40 thus includes a smooth and uniform membrane 49 having a hole or slit 43 therein. Further, an internal mating mechanism 45, such as a frusto-conical tapered mating mechanism made from a thickening of the port wall or a locking ring and taps, can be configured to mate with a distal end of the urine collection device 46.

Figure 9:
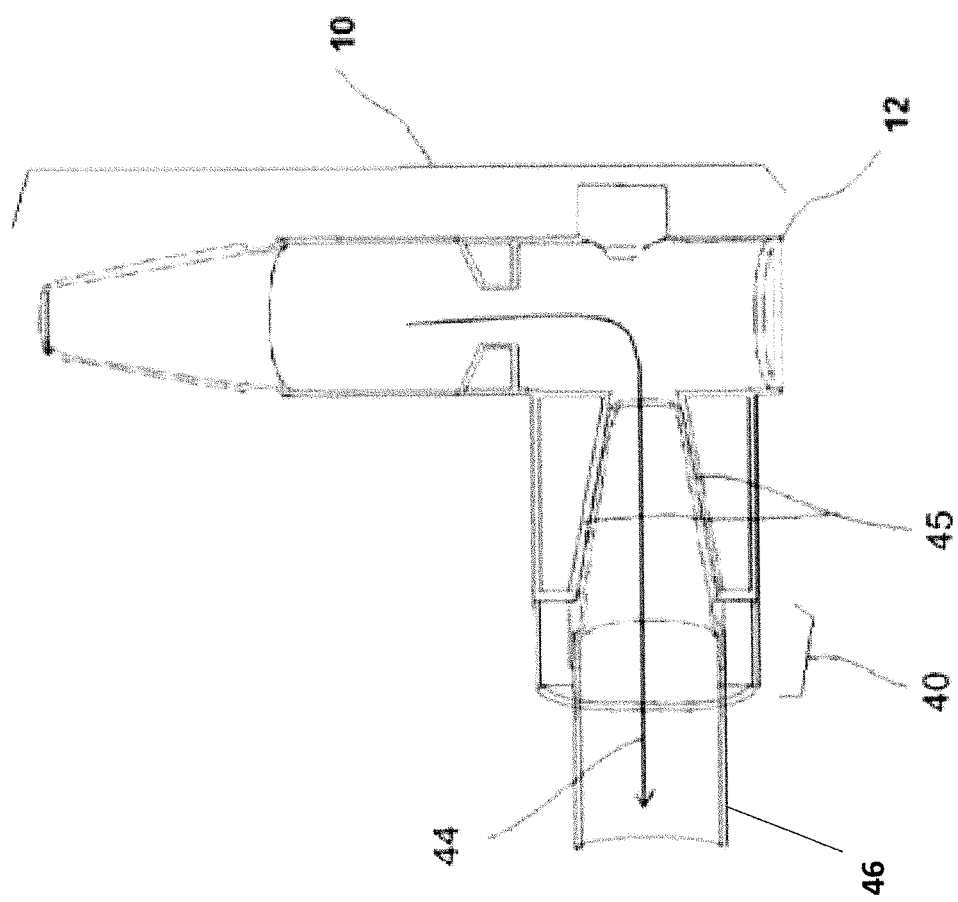
FIG. 9 is a cross section of the same embodiment of FIG. 8 showing the urine collection device connector connected to the port.

In use, the slit-valve 40 remains closed when the urinary collection device is disconnected, keeping the urinary catheter end of the system closed, and its sanitizable feature allows for aseptic re-connection of a urinary collection device 46. When the connecting end of a urinary collection device 46 is inserted into the slit 43 in the center of the slit-valve 40, the slit 43 opens by stretching around the connecting end. When fully inserted, the urinary connection device mates with the internal mating mechanism 45, which holds the connecting end firmly in the housing body until the user desires to disconnect the urinary collection device 46 from the catheter portion of the system. The slit-valve 40 and the internal mating mechanism 45 thus help to maintain an air and fluid tight seal. FIG. 9 illustrates a connected urinary collection device 46 attached to the connection 10 such that urine can flow (in direction of the arrow 44) into the urine collection device 46.

Figure 13B:
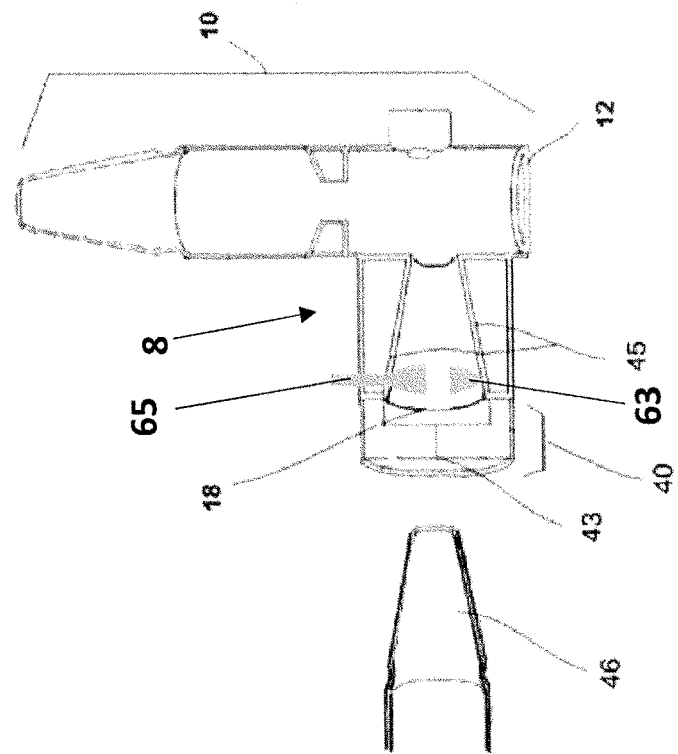
FIGS. 13A-13B show one embodiment of a port and valve assembly having an internal valve within the urine exit port.
Figure 13A:
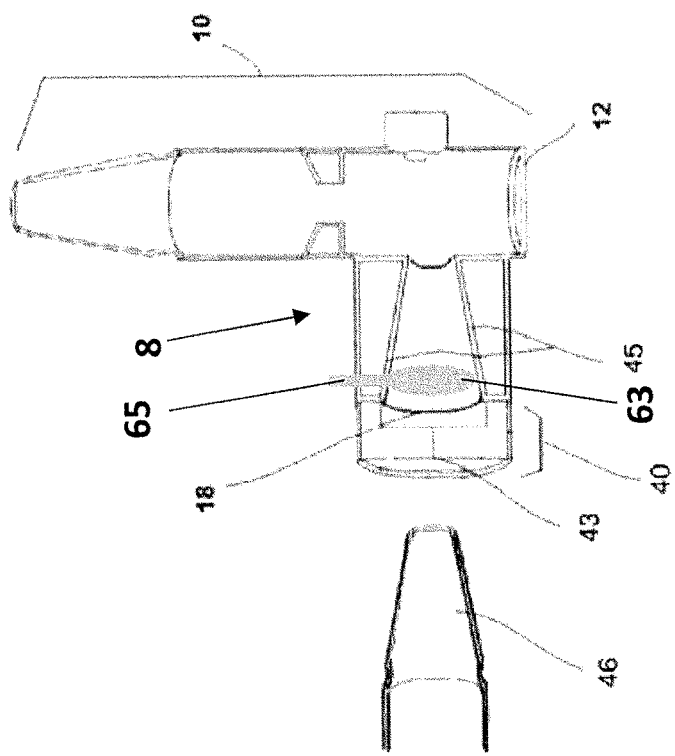

Further, referring to FIGS. 13A and 13B, in some embodiments, an internal valve 63, such as a spring valve or flap valve, can be positioned within the urine exit port 8 and be configured to allow urine to flow therethrough when open and to block the flow of urine when closed. In some embodiments, the internal valve 63 can be activated when the distal tip of the urine collection device 46 is inserted therethrough. In other embodiments, the internal valve can be configured to be activated manually to open or close the valve. For example, as shown in FIGS. 13A-13B, the valve can include an external dial 65 that, when rotated, can move the valve from closed (FIG. 13A) to open (FIG. 13B). For example, the internal valve 63 can be a stop cock or a deformable valve that, when squeezed orthogonally, opens the valve. Having an externally controlled valve 63 can advantageously allow the patient to close the valve when disconnecting from the urine collection device 46, but still open the valve when the patient wants to void into the toilet. In some embodiments, the internal valve 63 and the slit-valve 40 can be combined such that external activation of the internal valve opens the slit valve.

Figure 10B:
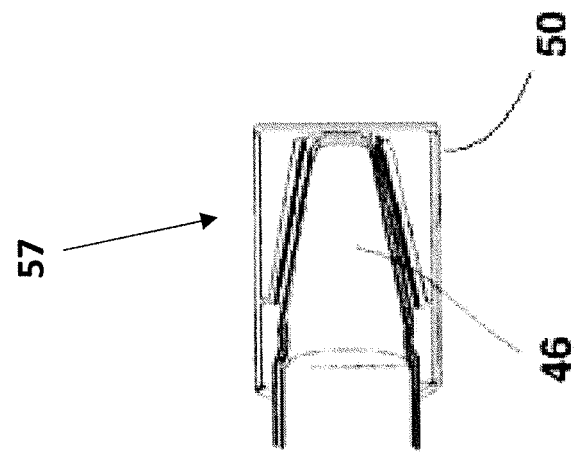
FIGS. 10A and 10B are cross sections of one embodiment of a sheath with a sanitizable slit membrane for protecting the connecting end of a urinary collection device when it is disconnected from the catheter end of the system.
Figure 10A:
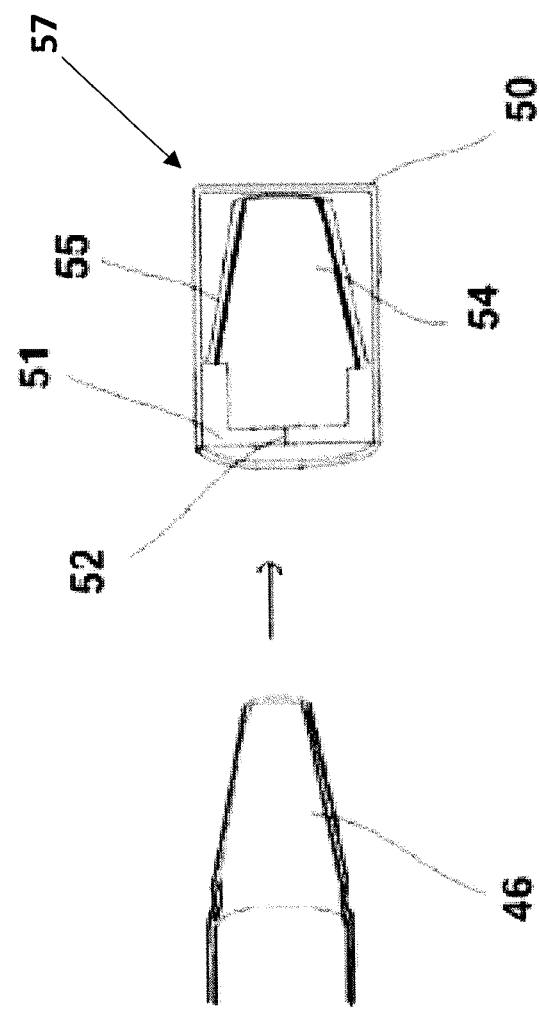

In some embodiments, a protective sheath or cap can be provided to cover a distal end of the urine collection device, i.e. the portion configured to connect to the assembly 10. FIG. 10A shows one embodiment of a protective sheath 57. The protective sheath 57 can include a rigid cylindrical housing 50 and an inner compartment 54 having a mating mechanism 55 configured to mate with a distal end of the urine collection device 46. Further, the mating mechanism 55 can be, for example, a frusto-conical tapered mating mechanism made from a thickening of the housing wall or a locking ring and taps. A slit-valve 51 can cover the proximal end of the cylindrical housing 50 to seal the inner compartment 54. The protective slit valve 51 can be similar in form and function to the valve 40 on the port and valve assembly, and as such, can be fully sanitizable and self-closing. Thus, when the urine collection device is not connected to the urine exit port 8 of the port and valve assembly 10 described herein, the connecting end of the urine collection device 46 can be inserted into the protective sheath 57 by pushing it through the slit-valve 51. The distal end of the device 46 can then mate with the inner compartment 54, where it can be maintained in an aseptic environment.

To aseptically disconnect the urine collection device 46 from the urine exit port 8 of the port and valve assembly 10 and connect it to the protective sheath 57 (e.g., to replace the drainage bag, etc.), the following steps are involved. Using aseptic techniques to assure no contamination of the device during transfer, the user first sanitizes the protective sheath slit-valve 51 with medical sanitizer. Next, the user disconnects the urine collection device 46 from the urine exit port 8 of the port and valve assembly 10 by pulling it proximally. The slit-valve 40 shuts tightly once the distal end of the urine collection device 46 is fully removed. The user can then push the distal edge of the urine collection device 46 against the slit-valve 51 to cause the slit 52 therein to open by expansion. The slit-valve 51 can maintain a tight seal around the distal end of the urine collection device 46, keeping the interior of the protective sheath closed off from the outside environment and aseptic. When the connecting end of the urinary collection device 46 is fully inserted into the protective sheath 57, it mates with mechanism 55 to hold the urinary collection device 46 firmly inside the protective sheath 57 until the user desires to remove it. When the user desires to disconnect the connecting end of the urine collection device 46 from the protective sheath 57 and connect to the urine exit port 8 of the port and valve assembly 10, the same basic process as above can be followed, first sanitizing the urine exit port slit-valve 40, disconnecting the connecting end of the urine collection device 46 from the sheath 57, and pushing the connecting end of the urine collection device 46 against the aseptic surface of valve 40 and into the assembly 10.

In some embodiments, an adaptor can be used to connect the distal end of the urinary collection device 46 to the assembly 10, thereby allowing one single optimized design of a port and valve assembly to be connected to various urinary collection devices even if the mating feature of the urinary collection device varies. The adaptor can be attached to the urine collection device to ensure compatibility between the collection device's connector and the port and valve assembly.

FIGS. 11A-C show an exemplary adaptor 80 configured to mate with both the distal end of a urinary collection device 46 and the urine exit port 8 of the port and valve assembly 10. The adaptor 80 can thus include a first connector 75 configured to mate with the distal end of the urine collection device 46 and a second connector 76 configured to mate with the urine exit port 8. The connectors 75, 76 can be, for example, frusto-conical tapered mating mechanisms or locking rings and taps. The adaptor 80 can further include a protective sheath 73 that extends over the connector 76. The sheath 73 can include accordion features or bellows 74 that enable the sheath 73 to retract when connected with the urine exit port 8 is desired. The material forming the bellows 74 can be made of a plastic, such as medical grade vinyl (PVC) or polyurethane, that has enough elasticity to allow the accordion to bend at its folds. The adaptor 80 can further include a protective slit membrane 70 that protects the adaptor mating tip of the second connector 76 and keeps it aseptic when the adaptor 80 is not connected to the port and valve assembly 10, as shown in FIG. 11A. FIG. 11B illustrates the adaptor 80 with the sheath 73 in its retracted state ready for connection, and FIG. 11C illustrates the adaptor 80 connected to the port and valve assembly 10, with connector 76 connected to the port 8.

In use, the adaptor 80 can be provided sterile to the user. Further, the adaptor 80 can be connected to the urinary collection device 46 upon first use and not disconnected from this junction throughout its use. The adaptor 80 advantageously allows for intermittent connection between the adaptor 80 and the port 8, keeping the urinary collection device 46 of the system aseptic when it is disconnected from the port and valve assembly 10. The only time the connector 76 is exposed to the outside of the system is when exposed for insertion into the urine exit port 8. This brief exposure can be performed using aseptic techniques, which when properly done, can ensure that the connector 76 is not exposed to any other contaminated surface. With the use of the slit membrane adaptor 80, the urinary collection device 46 is not exposed to the environment and is therefore protected from contamination whether disconnected or connected to the port and valve assembly 10.

FIGS. 12A-12B illustrates another exemplary adaptor 90. The adaptor 90 is similar to adaptor 80 except that retraction of the sheath 73 is provided by two rigid housings 72, 78 that are slidable relative to one another, i.e., in a telescoping fashion. A cylindrical connector 77 made, for example, of an elastic material or film, such as latex or polyurethane, can connect the distal end of the inner cylinder 72 with the proximal end of the outer cylinder 78. As shown in FIG. 12B, when the outer cylinder 78 moves proximally to expose the connector 76, the cylindrical connector 77 can stretch or unroll to maintain connection between the two cylinders 72, 78, thereby ensuring that no contaminants can get in between the cylinders 72, 78.

The sterile adaptors 80, 90 described herein can have multiple purposes. For example, the adaptor can advantageously ensure compatibility of the urine exit port of the port and valve assembly with the mating feature on the urinary collection device. The port and valve assembly can then be manufactured with a single connector design, while the adaptor can be customized for different potential types of urine collection device connectors (both present and future). The adaptor can also advantageously prevent contamination of the urine collection device while it is disconnected from the system.

In some embodiments, the port and valve assembly described herein is optimized such that patients can intermittently open the valve and slit membrane on the urine exit port to allow for discharge of urine from the catheter and bladder when a urine collection device is not used. This can be done by an internal mechanism that aseptically opens the urine exit port valve and slit membrane to allow for drainage, for example a stopcock valve that also splays open the slit membrane when open. In another embodiment, the features of the slit membrane and valve can be combined into a polymeric slit-valve that can be actuated by the patient to allow for urine discharge, for example by squeezing the slit-valve in a direction orthogonal to the slit. The patient could then void directly into the toilet, for example. Intermittent drainage from a slit-valve at the urine exit port of the port and valve assembly can also be achieved by insertion of a sterile external device into the urine exit port that allows for drainage. Packs of disposable sterile drainage tubes can be provided along with the port and valve assembly for situations when a urinary collection device is not used.

In some embodiments of the connector system, the inside walls of the port and valve assembly and/or of the adaptor may contain a coating that is saturated with an antiseptic agent such as nitrofurazone, silver salt, or other agent, as an added means of defense against micro-organism contamination. The contamination resistant coating may contain geometric features to deter biofilm formation, such as fractal patterns in the surface microstructure. In some embodiments, the contamination resistant features may be contained in the structural material itself, such as silver-containing micro-particles mixed into plastic.

The ports described herein can be configured to be large enough to connect to irrigation syringes and/or the typical connectors found in urinary drainage systems. For example, the ports can have a diameter of between ¼ inch and ½ inch, such as between ⅜ inch and 5/16 inch. These diameters can be larger than would be required for use, for example, with parenteral connectors.

Embodiments of the connector system here are shown as configured such that the catheter connection port and the irrigation and sampling port are in-line with one another along a central axis while the urinary collection port is orthogonal (approximately 90 degrees) to the central axis. This configuration can advantageously make irrigation and sampling more intuitive to the user and can allow the assembly to be attached to the patient so that gravity will drain urine into the urinary collection device. For example, for supine in-bed use, the assembly can be taped such that the in-line catheter connection and irrigation/sampling ports are along the leg, and the 90 degree drain from the urine exit port can be pointed toward the floor. In primarily ambulatory patients using a urine drainage bag, the assembly can be taped such that the urine exit port points down to the leg to the ground.

Advantageously, the systems, methods, and devices described herein can decrease the chance of urinary tract infection or bladder atony, decrease the risk of blood and body fluid exposure, greatly simplify the procedure of bladder irrigation, and allow for connection and disconnection of the urine collection device from the catheter end of the urinary drainage system while maintaining a closed aseptic system from the connecting end of the urine collection device to the bladder. The systems, methods, and devices described herein can also improve the quality of life of patients by allowing them more freedom from the urine collection device, allowing them to wear a catheter more discreetly during social interactions or when out of their home. Moreover, the systems, methods, and devices can improve the quality of life for caregivers who manage patients' catheters by making use of the device much easier and safer.

It will be apparent to a skilled artisan that the embodiments described herein are exemplary of inventions that may have greater scope than any of the singular descriptions presented. There may be alterations made in these examples without departing from the spirit and scope of the invention disclosed. For example, any aspect of an improved aseptic urinary drainage device and system may have components with different shapes or designs within different embodiments. For instance, spring types, housing shape, valve diameter and compositions may vary in design from one embodiment to another, but not overall function. In some embodiments, the catheter connection port may be the drainage end of a urinary catheter. In some embodiments, the urine exit port may be an intrinsic part of the urine collection device, and in some embodiments the port and valve assembly may be separate from the urine collection device. These or other features may change in different embodiments. In some embodiments, the shape or dimensions of the valves or mating and connection features may change, the housing shape, valve diameter and compositions may vary in design from one embodiment to another, but not in overall function.

What is claimed is:

1. A urinary catheter connector system comprising:
a housing;
a catheter connector port supported by the housing and configured to attach to a urinary catheter;
a urine exit port supported by the housing and configured to connect to a urine collection device;
an irrigation port supported by the housing and configured to receive an irrigation syringe, wherein the irrigation port includes a pliable membrane extending thereover, the pliable membrane having a self-sealing opening therein configured to allow a tip of the irrigation syringe to extend therethrough, wherein a proximal surface of the pliable membrane is flat and completely exposable to friction applied with a medical sanitizing agent so that the irrigation port is fully sanitizable;
a channel in the housing flidly connecting the catheter connector port, the urine exit port and the irrigation port; and
an internal valve supported by the housing and adapted to cooperate with the irrigation syringe to shut off flow of fluid and air to the urine exit port when the irrigation syringe is inserted and allow for flow of fluid and air to the urine exit port when the irrigation syringe is removed;
wherein a distance between a proximal surface of the membrane and a distal end of the internal valve is selected such that the tip of the irrigation syringe can extend from a proximal end of the self-sealing opening to the distal end of the internal valve when the irrigation syringe is inserted into the irrigation port.

2. The system of claim 1, wherein the internal valve comprises a valve seat adapted to mate with an exterior surface of the irrigation syringe to shut off the flow of fluid and air to the urine exit port when the irrigation syringe is inserted and allow for the flow of fluid and air to the urine exit port when the irrigation syringe is removed.

3. The system of claim 1, wherein the irrigation port connects to the channel between the catheter connection port and the urine exit port.

4. The system of claim 1, wherein the urine exit port includes a second pliable membrane extending thereover, the second pliable membrane including a second self-sealing opening therein configured to allow a tip of the urine collection device to extend therethrough.

5. A urinary catheter connector system comprising:
a housing;
a catheter connector port supported by the housing and configured to attach to a urinary catheter;
a urine exit port supported by the housing and configured to connect to a urine collection device;
an irrigation port supported by the housing and configured to receive an irrigation syringe, wherein the irrigation port includes a pliable membrane extending thereover, the pliable membrane having a self-sealing opening therein configured to allow a tip of the irrigation syringe to extend therethrough;
a channel in the housing fluidly connecting the catheter connector port, the urine exit port and the irrigation port; and
an internal valve supported by the housing and adapted to cooperate with the irrigation syringe to shut off flow of fluid and air to the urine exit port when the irrigation syringe is inserted and allow for flow of fluid and air to the urine exit port when the irrigation syringe is removed;
wherein the internal valve comprises a thickening in the wall of the housing, wherein the thickening decreases the diameter of the channel and is configured to approximate the size of the tip of the irrigation syringe and to mate snugly with the irrigation syringe, wherein when the irrigation syringe is inserted into the internal valve, the urine collection device is not in fluid communication with the catheter connector port, and when the syringe is not inserted into the internal valve, the urine collection device is in fluid communication with the catheter connector port;
further wherein a distance between a proximal surface of the membrane and a distal end of the internal valve is selected such that the tip of the irrigation syringe can extend from a proximal end of the self-sealing opening to the distal end of the internal valve when the irrigation syringe is inserted into the irrigation port.

6. The system of claim 5, wherein the pliable membrane is without crevices.

7. The system of claim 5, wherein the pliable membrane is smooth and uniform.

8. The system of claim 5, wherein the urine exit port includes a second pliable membrane extending thereover, the second pliable membrane including a second self-sealing opening therein configured to allow a tip of the urine collection device to extend therethrough.

9. A urinary catheter connector system comprising:
a housing;
a catheter connector port supported by the housing and configured to attach to a urinary catheter;
a urine exit port supported by the housing and configured to connect to a urine collection device, wherein the urine exit port includes a first pliable membrane extending thereover, the first pliable membrane having a self-sealing opening therein configured to allow a tip of a urine collection device connector to extend therethrough;
an irrigation port supported by the housing and configured to receive an irrigation syringe, wherein the irrigation port includes a second pliable membrane extending thereover, the second pliable membrane having a self-sealing opening therein configured to allow a tip of the irrigation syringe to extend therethrough;
an internal valve supported by the urine exit port housing and configured to allow flow of liquid through the urine exit port into the urine collection device when open and to shut off flow of liquid to the urine exit port when closed; and
a channel in the housing fluidly connecting the catheter connector port, the urine exit port and the irrigation port.

10. The urinary connector system of claim 9, wherein the internal valve is configured to be activated by the tip of the irrigation syringe.

11. The urinary connector system of claim 10, wherein the internal valve includes an external feature configured to allow manual activation of the valve.

12. The urinary connector system of claim 10, wherein the internal valve is a spring valve or a flap valve.

13. A urinary catheter connector system comprising:
   a housing;
   a catheter connector port supported by the housing and configured to attach to a urinary catheter;
   a urine exit port supported by the housing and configured to connect to a urine collection device, wherein the urine exit port includes a first pliable membrane extending thereover, the first pliable membrane having a self-sealing opening therein configured to allow a tip of a urine collection device connector to extend therethrough;
   an irrigation port supported by the housing and configured to receive an irrigation syringe, wherein the irrigation port includes a second pliable membrane extending thereover, the second pliable membrane having a self-sealing opening therein configured to allow a tip of the irrigation syringe to extend therethrough;
   a channel in the housing fluidly connecting the catheter connector port, the urine exit port and the irrigation port; and
   an adaptor including a proximal end configured to removably attach to the urine collection device and a distal end that includes the urine collection device connector.

14. The system of claim 13, wherein the adaptor includes a housing with a sanitizable slit membrane disposed over the distal end.

15. The system of claim 13, wherein the adaptor includes a sleeve covering the urine collection device connector, the sleeve configured to retract to expose the urine collection device connector.

16. The system of claim 15, wherein the sleeve includes accordion or telescoping features configured to allow the sleeve to retract.

17. The urinary connector system of claim 13, further comprising:
   an internal valve supported by the urine exit port housing and configured to allow flow of liquid through the urine exit port into the urine collection device when open and to shut off flow of liquid to the urine exit port when closed.

18. The system of claim 13, further comprising a rigid cap configured to cover and mate with the tip of the urine collection device connector, the rigid cap configured to be removed from the urine collection device connector for insertion of the connector into the urine exit port and to be replaced when the connector is removed from the urine exit port.

19. The system of claim 18, further comprising a slit-valve positioned over a proximal end of the rigid cap to seal an inner space within the rigid cap.

* * * * *

UNITED STATES PATENT AND TRADEMARK OFFICE
CERTIFICATE OF CORRECTION

PATENT NO. : 10,076,635 B2
APPLICATION NO. : 14/747972
DATED : September 18, 2018
INVENTOR(S) : Bradford Macy, Jr. et al.

Page 1 of 1

It is certified that error appears in the above-identified patent and that said Letters Patent is hereby corrected as shown below:

In the Claims

Column 17, Line 27, after "housing" and before "connecting" delete "flidly" and insert --fluidly--.

Signed and Sealed this
Fourth Day of June, 2019

Andrei Iancu
*Director of the United States Patent and Trademark Office*